United States Patent [19]
Choukroun et al.

[11] Patent Number: 5,767,217
[45] Date of Patent: Jun. 16, 1998

[54] PROCESS FOR THE PREPARATION OF POLYORGANOSILOXANES CONTAINING UNSATURATED FUNCTIONS, BY DEHYDROGENATIVE CONDENSATION IN THE PRESENCE OF TITANIUM, ZIRCONIUM OR HAFNIUM

[75] Inventors: Robert Choukroun, Toulouse; Jean-Marc Frances, Meyzieu; Frédérique Soleil, Toulouse, all of France

[73] Assignee: Rhone-Poulenc Chimie, Courbevoie Cedex, France

[21] Appl. No.: 617,798
[22] PCT Filed: Sep. 6, 1994
[86] PCT No.: PCT/FR94/01047
    § 371 Date: May 30, 1996
    § 102(e) Date: May 30, 1996
[87] PCT Pub. No.: WO95/07312
    PCT Pub. Date: Mar. 16, 1995

[30] Foreign Application Priority Data

Sep. 7, 1993 [FR] France ................... 93 10627

[51] Int. Cl.$^6$ ........................... C08G 77/08
[52] U.S. Cl. ................ 528/17; 528/18; 556/469; 556/466; 556/489
[58] Field of Search .......... 528/18, 17; 556/469, 556/466, 489

[56] References Cited

U.S. PATENT DOCUMENTS

| | | | |
|---|---|---|---|
| 2,970,150 | 1/1961 | Bailey et al. | 528/15 |
| 4,355,149 | 10/1982 | Koda et al. | 528/18 |
| 4,668,812 | 5/1987 | Quirk et al. | 556/466 |
| 4,780,337 | 10/1988 | Seyferth et al. | 427/387 |
| 5,087,719 | 2/1992 | Tilley et al. | 556/430 |
| 5,204,380 | 4/1993 | Seyferth et al. | 528/17 |

FOREIGN PATENT DOCUMENTS

| | | |
|---|---|---|
| 2033661 | 1/1971 | Germany . |
| 1365431 | 9/1974 | United Kingdom . |
| 9507312 | 3/1995 | WIPO . |

*Primary Examiner*—Melvyn I. Marquis
*Attorney, Agent, or Firm*—Burns, Doane, Swecker & Mathis, L.L.P.

[57] ABSTRACT

Provided is a process for the preparation of polyorganosiloxanes containing unsaturated functions. A polyorganohydrogenosiloxane (A) containing at least 0.1 mol % of hydrogen atoms linked directly to the silicon is reacted with at least a stoichiometric amount of a hydrocarbon compound (B) having at least one ethylenic or acetylenic unsaturation, in the presence of a catalytically effective amount of a dehydrogenative condensation catalyst comprising a metal complex of formula (I): $L_nMR_xY_y$. M represents a metal chosen from titanium, zirconium and hafnium; the symbols L are the same or different and represent a hydrocarbon ligand of the metal M, the said ligand donating from 3 to 8 π-electrons to the valence shell of the said metal; n is an integer ranging from 0 to 3; the symbols R are the same or different and represent a hydrocarbon or organosilicon ligand of the metal M, the ligand being a σ-electron donor; the symbols Y are the same or different and represent a ligand which forms, with the metal M, a covalent bond; x is an integer ranging from 0 to 4; y is an integer ranging from 0 to 4; the respective values of the numbers n, x and y being such that the number of electrons in the valence shell of the completed metal M is less than or equal to 18, wherein at least one of n, x and y does not equal zero.

14 Claims, No Drawings

PROCESS FOR THE PREPARATION OF POLYORGANOSILOXANES CONTAINING UNSATURATED FUNCTIONS, BY DEHYDROGENATIVE CONDENSATION IN THE PRESENCE OF TITANIUM, ZIRCONIUM OR HAFNIUM

The present invention relates to a process for the preparation of polyorganosiloxanes containing unsaturated functions, by dehydrogenative condensation of polyorganohydrogenosiloxanes and ethylenically and/or acetylenically unsaturated hydrocarbon compounds, in the presence of group IVA metal complexes (IUPAC).

According to the invention, this is a process for the preparation of polyorganosiloxanes containing unsaturated functions, characterized in that a polyorganohydrogenosiloxane (A) containing at least 0.1 mol %, preferably from about 1 mol % to 20 mol %, of hydrogen atoms linked directly to the silicon ("SiH") is reacted with at least a stoichiometric amount of a hydrocarbon compound (B) having at least one ethylenic or acetylenic unsaturation, in the presence of a catalytically effective amount of a dehydrogenative condensation catalyst consisting of a complex of a group IV metal of formula (I)

$$L_n MR_x Y_y \qquad (I)$$

in which formula
M represents a group IV metal (IUPAC)
the symbols L are the same or different and represent a hydrocarbon ligand of the metal M, the said ligand donating from 3 to 8 π-electrons to the valence shell of the said metal;
n is an integer ranging from 0 to 3;
the symbols R are the same or different and represent a hydrocarbon or organosilicon ligand of the metal M, the said ligand being a σ-electron donor;
the symbols Y are the same or different and represent a ligand which forms, with the metal M, a covalent bond;
x is an integer ranging from 0 to 4;
y is an integer ranging from 0 to 4;
wherein at least one of n, x and y does not equal zero;
the respective values of the numbers n, x and y being such that the number of electrons in the valence shell of the complexed metal M is less than or equal to 18 and preferably greater than or equal to 8.

Among the group IV metal complexes of formula (I) which may be used as dehydrogenative condensation catalyst, mention may be made of the titanium, zirconium or hafnium complexes.

Among the ligands L which may be mentioned are the $\eta^3$-allyl, $\eta^5$-cyclopentadienyl and $\eta^7$-cycloheptatrienyl which may or may not be substituted, $\eta^6$ aromatics such as substituted or unsubstituted $\eta^6$ benzene, and the like.

Among the ligands R which may be mentioned are $C_1$–$C_8$ alkyl groups, $C_6$–$C_{12}$ aryl groups, and the like.

Among the ligands Y which may be mentioned are hydrogen atoms, halogen atoms (chlorine, fluorine, bromine and iodine), $C_1$–$C_4$ alkoxy groups, and the like.

As examples of complexes, mention may be made of
bis(cyclopentadienyl)di-1-butylzirconium
tetrabenzylzirconium
tetraneopentylzirconium
butoxytris((trimethylsilyl)methyl)zirconium
dinorbornyldimethyltitanium
bis(cyclopentadienyl)dimethylzirconium
cyclopentadienyltribenzylzirconium
cyclopentadienyltrimethyltitanium
cyclopentadienyltrimethylzirconium
bis(cyclopentadienyl)dineopentyltitanium
cyclopentadienyldiphenylisopropoxyzirconium
((trimethylsilyl)cyclopentadienyl)trimethylzirconium
bis(cyclopentadienyl)bis(trimethylsilyl)zirconium
bis(cyclopentadienyl)dihydrogenozirconium
bis(cyclopentadienyl)dihydrogenotitanium
bis(cyclopentadienyl)chlorohydrogenozirconium
bis(cyclopentadienyl)butylhydrogenozirconium
bis(cyclopentadienyl)methylhydrogenozirconium The said polyorganohydrogenosiloxane (A) used may be linear, cyclic or three-dimensional. It contains units, which are the same or different, of formula (II)

$$R'_a H_b SiO_{(4-a-b)/2} \qquad (II)$$

where
the symbols R', which are the same or different, represent a $C_1$–$C_{18}$ alkyl group, a vinyl group or a $C_6$–$C_{12}$ aryl or aralkyl group, optionally substituted with halogen atoms (fluorine in particular), preferably at least 60 mol % of the said radicals R' representing a methyl group;
a is equal to 0, 1, 2, or 3;
b is equal to 0 or 1;
a+b=0, 1, 2 or 3;
the content of $SiO_{4/2}$ units being less than 30 mol % the number of units of formula (II) in which b is other than 0 being such that the said polyorganohydrogenosiloxane (A) contains at least 0.1 mol %, preferably about 1 mol % to 20 mol %, of hydrogen atoms linked directly to the silicon ("SiH").

This polyorganohydrogenosiloxane is preferably liquid; its dynamic viscosity at 25° C. may be up to 1.000.000 mPa s; this viscosity is generally from about 1 to 10.000 mPa s.

The dynamic viscosity at 25° C. of the silicone polymers may be measured using a Brookfield viscometer according to the AFNOR standard NFT 76 102 of February 1992.

Among the unsaturated hydrocarbon compounds (B) which may be used, mention may be made of linear or branched $C_2$–$C_{24}$ alkenes, $C_6$–$C_{12}$ cycloalkenes, linear or branched $C_2$–$C_{24}$ alkynes, optionally substituted with one or more halogen atoms and/or with one or more $C_6$–$C_{12}$ aryl groups, saturated esters of ethylenically unsaturated carboxylic acids, unsaturated esters of saturated carboxylic acids, organosilanes or organosiloxanes bearing ethylenic or acetylenic unsaturated groups, and the like.

By way of example, mention may be made of: ethylene, 1-octene, 1,4-butadiene, 1,5-hexadiene, 1,9-decadiene, perfluoro olefins of formula $CF_3$—$(CF_2)_{0-5}$—$(CH_2)_{0-6}$—$CH=CH_2$, 1,5-cyclooctadiene, acetylene, 1-hexyne, styrene, ethyl acrylate, vinyltrimethylsilane, 1,3-divinyltetramethyldisiloxane, cyclopentadiene and the dimer, and the like.

In the definition of a mole of polyorganohydrogenosiloxane (A), a hydrogen atom linked directly to the silicon ("SiH") will be considered as the elemental species.

In the definition of a mole of unsaturated hydrocarbon compound (B), an ethylenic or acetylenic unsaturation capable of forming, with an "SiH" function of (A), a dehydrogenating coupling will be considered as the elemental species.

By way of example, the reaction scheme for dehydrogenative condensation is as follows when the unsaturated hydrocarbon compound (B) is an alpha-olefin:

$$Si-H \text{ [of (A)]} + H_2C=CH-R'' \text{ [of (B)]} \rightarrow Si-CH=CH-R''+H_2$$

The said process forming the subject of the invention is favourably performed using an excess of constituent (B)

relative to the stoichiometry. This excess preferably corresponds to a (B)/(A) molar ratio of about 1.1 to 100, preferably of about 1.1 to 10.

The expression catalytically effective amount of dehydrogenative condensation catalyst is understood to refer to an amount which is sufficient to ensure a suitable dehydrogenative condensation reaction.

The said catalyst is generally used in amounts from about $1 \cdot 10^{-5}$ mol to 0.5 mol, preferably from about $1 \cdot 10^{-4}$ mol to 0.1 mol, per 100 mol of polyorganohydrogenosiloxane (A).

The preparation of the catalyst or complex of formula (I) is based on the chemical reduction of a suitable precursor of the complex of formula (I), this precursor itself being in the form of a halogenated metal complex, by magnesium in the presence of THF (tetrahydrofuran) or by alkyllithiums in solution in a saturated hydrocarbon. Other reducing agents such as Li—, Na— or K—M (M=naphthalene), M'BH$_4$, (M'=Li, Na or K), an alkyl-Mg-halogen compound, NaAlH, (OCH$_2$CH$_2$OCH$_3$)$_2$, LiAlH$_4$, LiAlH(alkoxy)$_3$, LiHBR$_3$, MgH$_2$, Al, Zn or AlCl$_{3-z}$(R)$_z$, with Z being an integer ranging from 0 to 2, may be used.

The dehydrogenative condensation operation may be performed at a temperature from about 0° to 200° C., preferably from about 20° to 150° C.

A solvent may be present to decrease the viscosity of the medium; examples which may be mentioned are aromatic, aliphatic or cycloaliphatic hydrocarbons such as toluene, hexane and cyclohexane, and the like.

The examples which follow are given by way of illustration and cannot be considered as a limitation of the field or spirit of the invention.

EXAMPLE 1

The following are introduced into a 250 cm$^3$ three-necked round-bottomed flask at room temperature:

$2 \cdot 10^{-4}$ mol of Cp$_2$ZrCl$_2$ $(_{Cp=\eta}{}^5$-cyclopentadienyl)

15 ml of toluene de-aerated under argon $3.8 \cdot 10^{-4}$ mol of butyllithium in the form of a solution in hexane containing 1.6 mol of lithium per liter, which corresponds to a BuLi/Cp$_2$ZrCl$_2$ molar ratio of 1.9.

The catalytic medium is left at room temperature with magnetic stirring for 20 min. 4.1 g of α,ω-dimethylhydrogenosilyl polydimethylsiloxane of molecular weight (Mn=1022), i.e. $8 \cdot 10^{-3}$ mol of hydrogenosilyl function, are then added very rapidly.

230 cm$^3$ of ethylene, i.e. $9.5 \cdot 10^{-3}$ mol of ethylene, are subsequently added at atmospheric pressure.

The medium is maintained at 100° C. for 7 hours and a clear reaction medium is recovered. The toluene is removed under 30 Pa at 75° C. The polymer obtained is subsequently analyzed by $^1$H NMR.

A degree of conversion of 100% of the SiH units is observed, as well as the formation of a polymer of α,ω-dimethylvinyl polydimethylsiloxane structure. The proportion of hydrogenated vinyl units is less than 5 mol %.

EXAMPLE 2

The operation described in Example 1 is repeated over 5 hours at 90° C. using a catalyst content of $2.3 \cdot 10^{-4}$ mol, the BuLi/Cp$_2$ZrCl$_2$ ratio still being 1.9.

The degree of conversion of the SiH units is 81%.
$^{29}$Si NMR analysis reveals 75 mol % of SiVi units 15 mol % of Si—CH$_2$—CH$_3$ units 10 mol % of Si—CH$_2$—CH—Si units

EXAMPLE 3

$2.36 \cdot 10^{-4}$ mol of Cp$_2$ZrCl$_2$, 5 ml of toluene and $4.48 \cdot 10^{-4}$ mol of butyllithium are introduced into a 25 ml round-bottomed flask. The mixture is left stirring for 25 min at 20° C. $1.98 \cdot 10^{-2}$ mol of freshly distilled styrene and the α,ω-dimethylhydrogenosilyl polydimethylsiloxane of Example 1 in an amount corresponding to $9 \cdot 10^{-3}$ mol of hydrogenosilyl functions are added. The medium is heated at 95°–100° C. for 7 hours. The oil obtained after evaporation is analysed by $^1$H NMR.

The degree of conversion of the hydrogenosilyl functions is 100%. More than 90 mol % of an oil corresponding to the following average structure is obtained:

trans Ph—CH=CH—Si (Me)$_2$—O—[Si (Me)$_2$—O]$_{12}$—Si (Me)$_2$ —CH=CH—Ph (Ph=phenyl; Me=methyl)

EXAMPLE 4

The following are introduced into a 25 ml three-necked round-bottomed flask:

$2.4 \cdot 10^{-3}$ mol of Cp$_2$ZrCl$_2$ 15 ml of toluene $4.6 \cdot 10^{-3}$ mol of butyllithium The catalytic medium is left stirring at room temperature under argon for 1 hour.

A mixture containing 3 g of the α,ω-dimethylhydrogenosilyl polydimethylsiloxane described in Example 1 (i.e. $6 \cdot 10^3$ mol of hydrogenosilyl functions) and 13.5 g of 1-octene (i.e. $0.12 \cdot 10^{-1}$ mol) is then added.

The medium is maintained at 90° C. for 7 hours. The excess octene and the toluene are removed under a vacuum of 500 Pa at 50° C.

Analysis of the oil by $^1$H NMR and $^{29}$Si NMR indicates the predominant formation of an α,ω-octenyl polymethylsiloxane oil.

The degree of conversion of the hydrogenosilyl units is greater than 95%.

$^{29}$Si NMR analysis in (CH$_3$)$_4$Si as solvent reveals the following chemical shifts δ in ppm (parts per million):

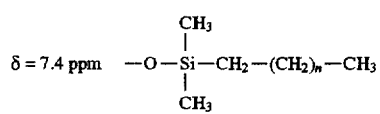

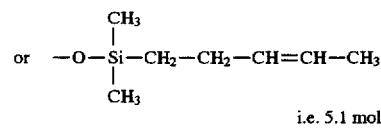

i.e. 5.1 mol%

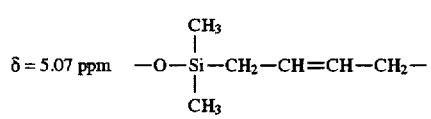

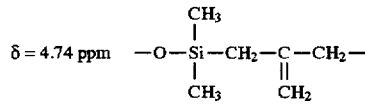

i.e. 7.4 mol%

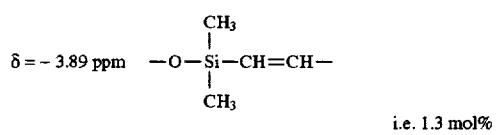

i.e. 1.3 mol%

$\delta = -20.7 \text{ to} -22.6 \text{ ppm}$  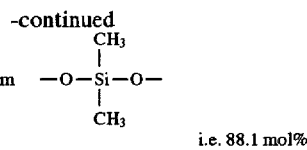

i.e. 88.1 mol%

EXAMPLE 5

The catalyst is prepared from a stock solution of $Cp_2ZrCl_2$ (0.150 g, $5.13\ 10^{-4}$ mol) and Mg (0.052 g, $2.14\ 10^{-3}$ mol) in 6 ml of TEF in the presence of 1.3 g of styrene $PhCH=CH_2$ (i.e. $1.25\ 10^{-2}$ mol). The solution is stirred at room temperature for 3 hours and the final solution is red in colour.

a)

1.5 ml of the above stock solution, i.e. $1.03\ 10^{-4}$ mol of $Cp_2ZrCl_2$ (0.030 g), 5 ml of THF, 2.42 g of styrene (2.32 $10^{-2}$ mol, i.e. $2.58\ 10^{-2}$ mol in total) and 5.16 g of the siloxane compound of Example 1 (5.16 g, i.e. $1.03\ 10^{-2}$ mol of SiH) are successively introduced into a 50 ml Schlenk tube. The solution is heated at 90° C. for 10 hours. A clear solution is recovered. After evaporation of THF from the solution, $^1$H NMR in $CDCl_3$ of the siloxane oil shows protons corresponding to the trans grafting of styrene onto the Si—H bonds of the starting oil, by dehydrogenative condensation, and the disappearance of the peaks relating to the Si—H of the starting oil. A polydimethylsiloxane oil of the following average formula is obtained:

Ph—CH=CH—SiMe$_2$—[SiMe$_2$O]$_{12}$—SiMe$_2$—CH=CH—Ph

The degree of conversion of the Si—H bonds is 100% for an [Si—H]/[catalyst] ratio a 100, [styrene]/[SiH] ratio=2.74.

b)

The same experimental process was used for 5.20 g of styrene (5 $10^{-2}$ mol, i.e. $5.25\ 10^{-2}$ mol in total), 10.2 g of the α,ω-hydrogenodimethylsilyl polydimethylsiloxane of Example 1 ($2.04\ 10^{-2}$ mol of SiH) and addition of 15 ml of THF.

The degree of conversion of the Si—H bonds is 100% for an [Si—H]/[catalyst] ratio a 198, [styrene]/[SiH] ratio=2.7.

c)

The same experimental process was used for 4.23 g of styrene ($4.07\ 10^{-2}$ mol, i.e. $4.33\ 10^{-2}$ mol in total), 2.88 g of a polypolydimethylmethylhydrogenosiloxane oil of average formula Me$_3$SiO—[SiMe$_2$O]$_{9,1}$—[SiMe(H)O]$_{4}$—SiMe$_3$ (i.e. $1.07\ 10^{-2}$ mol of SiH) and addition of 5 ml of THF.

The degree of conversion of the Si—H bonds is 100% for an [SiH]/[catalyst] ratio=103, [styrene]/[SiH] ratio=4.29. An oil of average formula Me$_3$SiO—[SiMe$_2$O]$_{9,1}$—[Si(Me)(—CH=CH—Ph)—O]$_4$—SiMe$_3$ is obtained.

d)

The same experimental process was used for 8.34 g of styrene (8 $10^{-2}$ mol, i.e. $8.27\ 10^{-2}$ mol in total), 5.56 g of the polymethylhydrogenosiloxane described in Example 5-c) (i.e. $2.06\ 10^{-2}$ mol of SiH) and addition of 5 ml of THF.

The degree of conversion of the Si—H bonds is 100% for an [SiH]/[catalyst] ratio=200, [styrene]/[SiH] ratio=4.13 and the same polymer is obtained as that described in Example 5-c.

EXAMPLE 6

The catalyst is prepared from a stock solution of $Cp_2ZrCl$. (0.230 g, $7.87\ 10^{-4}$ mol) and Mg (0.099 g, $4.07\ 10^{-3}$ mol) in 20 ml of THF. The solution is stirred at room temperature for 24 hours and the final solution is red in colour.

The experimental process is then the same as for Example 5, with a reaction time of 48 h at 90° C.

a)

2 ml of the stock solution (i.e. $7.86\ 10^{-5}$ mol of catalyst), 1.18 g of styrene ($1.13\ 10^{-3}$ mol), 1.86 g of hydrogenosilicone described in Example 1 ($3.72\ 10^{-3}$ mol of SiH) and 5 ml of THF were used.

The degree of conversion of the Si—H bonds is 100% for an Si-[H]/[catalyst] ratio=47, [styrene]/[SiH] ratio=3. The polymer of the following average formula is indeed obtained:

Ph—CH=CH—SiMe$_2$—[SiMe$_2$O]$_{12}$—SiMe$_2$—CH=CH—Ph b)

3 ml of the stock solution (i.e. $1.18\ 10^{-4}$ mol of catalyst), 17.8 g of styrene (0.171 mol), 9.26 g of the polydimethylmethylhydrogenosiloxane oil of average formula Me$_3$SiO—[SiMe$_2$O]$_{9,1}$—[SiMe(H)O]$_4$—SiMe$_3$ (i.e. $3.43\ 10^{-2}$ mol of SiH) and 15 ml of THF were used.

The degree of conversion of the Si—H bonds is 94% for an [Si—H]/[catalyst] ratio=290, [styrene]/[SiH] ratio=4.98.

c)

1.5 ml of the stock solution (i.e. $5.9\ 10^{-5}$ mol of catalyst), 5.6 g of styrene ($5.36\ 10^{-2}$ mol), 9.16 of silicone described in Example 1 (i.e. $1.83\ 10^{-2}$ mol of SiH) and 10 ml of THF were used.

The degree of conversion of the Si—H bonds is 100% for an [Si—H]/[catalyst] ratio=350, [styrene]/[Si—H] ratio= 2.93. The oil of the following average formula is indeed obtained selectively:

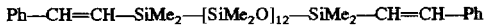
Ph—CH=CH—SiMe$_2$—[SiMe$_2$O]$_{12}$—SiMe$_2$—CH=CH—Ph

EXAMPLE 7

The catalyst is prepared from a stock solution of $Cp_2ZrCl_2$ (0.105 g, $3.59\ 10^{-4}$ mol) and Mg (0.065 g, $2.67\ 10^{-3}$ mol) in 5 ml of THF. The solution is stirred at room temperature for 24 hours and the final solution is red in colour. 7 ml of ThF and the siloxane oil described in Example 1 (2.6 g, $5.2\ 10^{-3}$ mol of SiH) are added to 2 ml of this solution. This red mixture is introduced into a predried autoclave under vacuum and is brought to a temperature of 90° C. under an ethylene atmosphere. An ethylene $C_2H_4$ supply line fitted with a pressure regulator makes it possible to set and keep constant the ethylene pressure in the reactor. This pressure is then set to 5 bar of $C_2H_4$ with a reaction time of 12 h at 90° C.

The degree of conversion of the Si—H bonds of the starting oil is 100% for an [Si—H]/[catalyst] ratio=36. $^1$H NMR and $^{29}$Si NMR analysis of the oil obtained shows that an oil of the following average formula is obtained:

H$_2$C=CH—SiMe$_2$—[SiMe$_2$O]—SiMe$_2$—CH=CH$_2$

The molar percentage of SiVi functions is greater than 95%.

EXAMPLE 8

The following are successively introduced into a 100 ml Schlenk tube under argon: 0.048 g of $Cp_2ZrCl_2$ ($1.64\ 10^{-4}$ mol); 0.022 g of magnesium ($9.5\ 10^{-4}$ mol); 10 ml of tetrahydrofuran; 3.4 g of styrene (i.e. $3.27\ 10^{-2}$ mol); 2.2 g of the polydimethylmethylhydrogenosiloxane hydrogenated silicone oil of average formula

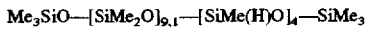
Me$_3$SiO—[SiMe$_2$O]$_{9,1}$—[SiMe(H)O]$_4$—SiMe$_3$ (i.e. $8.15\ 10^{-3}$ mol SiH). The mixture is heated at 90° C. for 15 hours. The reaction mixture is allowed to cool to room temperature and is analysed by NMR. The oil obtained corresponds to a degree of conversion of 100% of the hydrogenosilyl functions SiH and has an average formula:

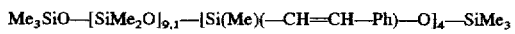

What is claimed is:

1. A process for the preparation of polyorganosiloxanes containing unsaturated functions, wherein a polyorganohydrogenosiloxane (A) containing at least 0.1 mol % of hydrogen atoms linked directly to the silicon is reacted with at least a stoichiometric amount of a hydrocarbon compound (B) having at least one ethylenic or acetylenic unsaturation, in the presence of a catalytically effective amount of a dehydrogenative condensation catalyst comprising a metal complex of formula (I)

in which formula

M represents a metal chosen from titanium, zirconium and hafnium the symbols L are the same or different and represent a hydrocarbon ligand of the metal M, the said ligand donating from 3 to 8 π-electrons to the valence shell of the said metal;

n is an integer ranging from 0 to 3;

the symbols R are the sate or different and represent a hydrocarbon or organosilicon ligand of the metal M, the said ligand being a σ-electron donor;

the symbols Y are the same or different and represent a ligand which forms, with the metal M, a covalent bond;

x is an integer ranging from 0 to 4;

y is an integer ranging from 0 to 4;

the respective values of the numbers n, x and y being such that the number of electrons in the valence shell of the completed metal M is less than or equal to 18, wherein at least one of n, x and y does not equal zero.

2. The process according to claim 1, wherein the (B)/(A) molar ratio is from about 1.1 to 100.

3. The process according to claim 1, wherein the polyorganohydrogenosiloxane (A) is linear, cyclic or three-dimensional and contains units, which are the same or different, of formula (II)

where the symbols R', which are the same or different, represent a $C_1$-$C_{18}$ alkyl group, a vinyl group or a $C_1$-$C_{12}$ aryl or aralkyl group, optionally substituted with halogen atoms;

a is equal to 0, 1, 2, or 3;

b is equal to 0 or 1;

a+b=0, 1, 2 or 3;

the content of $SiO_{4/2}$ units being less than 30 mol % the number of units of formula (II) in which b is other than 0 being such that the said polyorganohydrogenosiloxane (A) contains at least 0.1 mol %, of hydrogen atoms linked directly to the silicon.

4. The process according to claim 3, wherein at least 60 mol % of the radicals R' represents a methyl group.

5. The process according to claim 1, wherein the unsaturated hydrocarbon compound (B) is a linear or branched $C_2$-$C_{24}$ alkene, a $C_6$-$C_{12}$ cycloalkene, a linear or branched $C_2$-$C_{24}$ alkyne, optionally substituted with one or more halogen atoms and/or with one or more $C_6$-$C_{12}$ aryl groups, a saturated ester of an ethylenically unsaturated carboxylic acid, an unsaturated ester of a saturated carboxylic acid, or an organosilane or organosiloxane bearing ethylenic or acetylenic unsaturated groups.

6. Process according to any one of claims 2–5 or 1, characterized in that the respective values of n, x, and y in the complex of formula (I) are such that the number of electrons in the valence shell of the complexed metal M is greater than or equal to 8.

7. The process according to claim 1, wherein the respective values of n, x, and y in the complex of formula (I) are such that the number of electrons in the valence shell of the complexed metal M is greater than or equal to 8.

8. The process according to claim 1, wherein the ligands L of the complex of formula (1) are $\eta^3$-allyl, $\eta^5$-cyclopentadienyl or $\eta^7$-cycloheptatrienyl which may or may not be substituted, or substituted or unsubstituted $\eta^6$ aromatics.

9. The process according to claim 1, wherein the ligands R of the complex of formula (I) are $C_1$-$C_8$ alkyl groups or $C_6$-$C_{12}$ aryl groups.

10. The process according to claim 1, wherein the ligands Y of the complex of formula (I) are hydrogen atoms, halogen atoms or $C_1$-$C_4$ alkoxy groups.

11. The process according to claim 1, wherein the said complex of formula (1) is bis(cyclopentadienyl)di-1-butylzirconium tetrabenzylzirconium tetraneopentylzirconium butoxytris((trimethylsilyl)methyl)zirconium dinorbornyldimethyltitanium bis(cyclopentadienyl)dimethylzirconium cyclopentadienyltribenzylzirconium cyclopentadienyltrimethyltitanium cyclopentadienyltrimethylzirconium bis(cyclopentadienyl)dineopentyltitanium cyclopentadienyldiphenylisopropoxyzirconium ((trimethylsilyl)cyclopentadienyl)trimethylzirconium bis(cyclopentadienyl)bio(trimethylsilyl)zirconium bis(cyclopentadienyl)dihydrogenozirconium bis(cyclopentadienyl)dihydrogenotitanium bis(cyclopentadienyl)chlorohydrogenozirconium bis(cyclopentadienyl)butylhydrogenozirconium or bis(cyclopentadienyl)methylhydrogenozirconium.

12. The process according to claim 1, wherein the said complex of formula (I) is used in amounts from about 1 $10^{-5}$ mol to 0.5 mol per 100 mol of polyorganohydrogenosiloxane (A).

13. The process according to claim 12, wherein the complex of formula (I) is used in amounts from about 1 $10^{-4}$ mol to 0.1 mol per 100 mol of polyorganohydrogenosiloxane (A).

14. The process according to claim 1, wherein the complex of formula (I) is prepared by chemical reduction of a precursor in the form of a halogenated metal complex using a reducing agent selected from the group consisting of: magnesium in the presence of THF (tetrahydrofuran); alkyllithiums in solution in a saturated hydrocarbon; Li—, Na— or K—M (M=naphthalene); M'$BH_4$ (M'=Li, Na or K); an alkyl-Mg-halogen compound; $NaAlH_2$ $(OCH_2CH_2OCH_3)$ 2; $LiAlH_4$, $LiAlH(alkoxy)_3$; $LiHBR_3$; $MgH_2$; Al; Zn; $AlCl_{3-z}(R)_z$ with being an integer ranging from 0 to 2.

* * * * *